United States Patent [19]

Herrmann et al.

[11] Patent Number: 5,329,926
[45] Date of Patent: Jul. 19, 1994

[54] THERAPY STATION FOR TREATMENT WITH FOCUSED ACOUSTIC WAVES HAVING AN X-RAY LOCATING SYSTEM PIVOTABLE RELATIVE TO AN ACOUSTIC WAVE SOURCE

[75] Inventors: Klaus Herrmann, Nuremberg; Guenther Krauss, Erlangen; Peter Noegel, Effeltrich, all of Fed. Rep. of Germany

[73] Assignee: Siemens Aktiengesellschaft, Munich, Fed. Rep. of Germany

[21] Appl. No.: 100,371

[22] Filed: Aug. 2, 1993

[30] Foreign Application Priority Data

Sep. 29, 1992 [DE] Fed. Rep. of Germany ....... 4232683

[51] Int. Cl.$^5$ .......................... A61B 6/00; A61B 17/22
[52] U.S. Cl. ........................................ 128/653.1; 601/3
[58] Field of Search ............ 128/24 EL, 660.03, 653.1

[56] References Cited

U.S. PATENT DOCUMENTS

| | | |
|---|---|---|
| 4,674,505 | 1/1987 | Pauli et al. . |
| 4,697,588 | 10/1987 | Reichenberger . |
| 4,796,613 | 1/1989 | Heumann et al. ............. 128/24 EL |
| 4,926,857 | 5/1990 | Wessels . |
| 4,976,255 | 12/1990 | Reichenberger et al. . |
| 5,044,354 | 9/1991 | Goldhorn et al. . |
| 5,060,650 | 10/1991 | Wurster et al. ................ 128/24 EL |
| 5,065,741 | 11/1991 | Uchiyama et al. ............. 128/24 EL |

FOREIGN PATENT DOCUMENTS 9005492 5/1990 PCT Int'l Appl. ............ 128/24 EL

*Primary Examiner*—Ruth S. Smith
*Attorney, Agent, or Firm*—Hill, Steadman & Simpson

[57] ABSTRACT

A therapy station for treatment of a patient with focused acoustic waves has a source of focused acoustic waves attached to a source carrier, an x-ray carrier carrying an x-ray locating system, and a support table for the patient. The x-ray carrier is pivotably attached to the source carrier so as to be pivotable relative to the source of acoustic waves and such that the central ray of the x-ray locating system always proceeds through the focus of the focused acoustic waves, and the source carrier is adjustable relative to the support table in a plane.

9 Claims, 1 Drawing Sheet

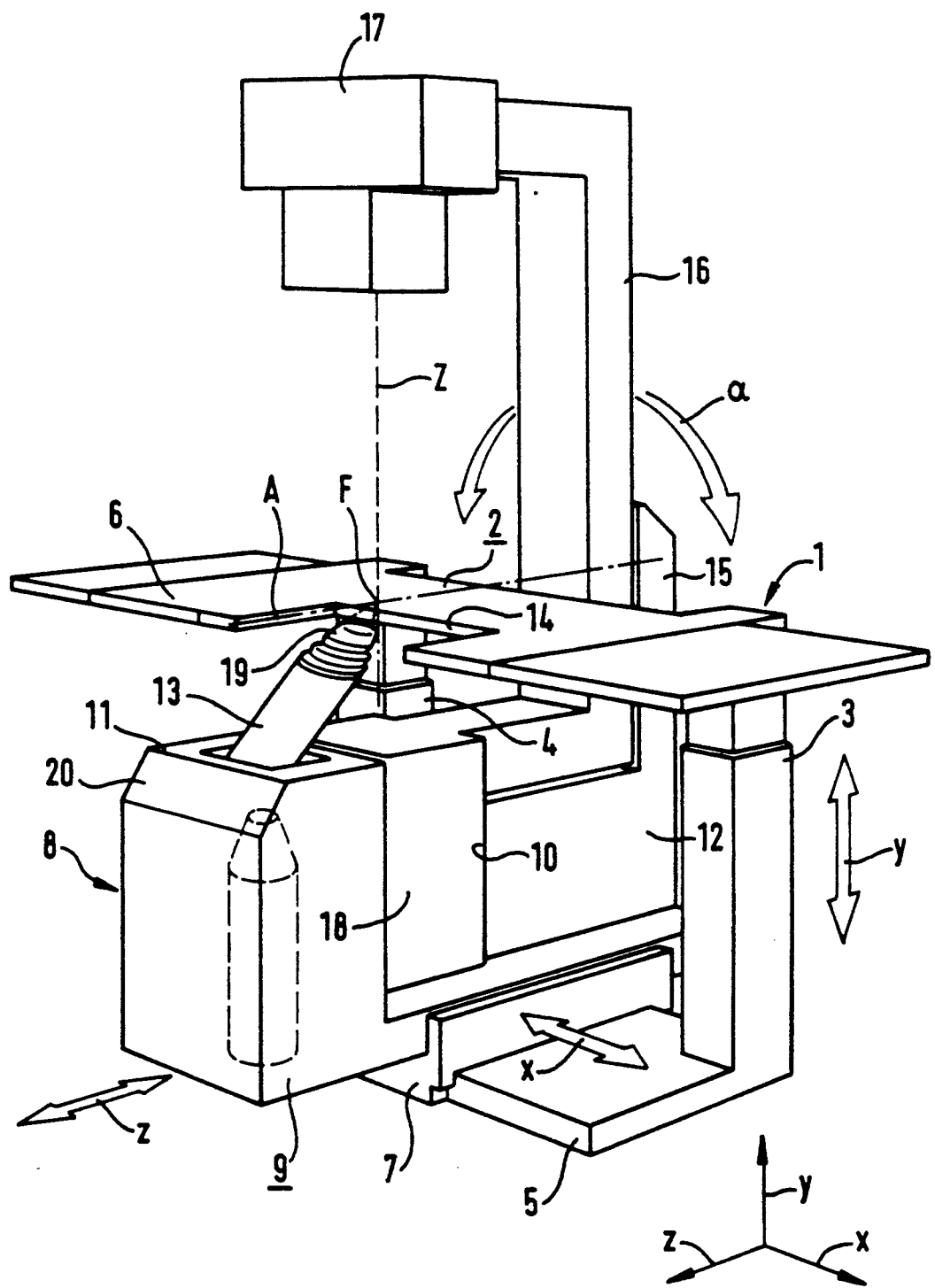

THERAPY STATION FOR TREATMENT WITH FOCUSED ACOUSTIC WAVES HAVING AN X-RAY LOCATING SYSTEM PIVOTABLE RELATIVE TO AN ACOUSTIC WAVE SOURCE

BACKGROUND OF THE INVENTION

1. Field of the Invention

The present invention is directed to a therapy station for treatment of a patient with focused acoustic waves, of the type including a source carrier to which a source of focused acoustic waves is attached, an x-ray carrier to which an x-ray locating system is attached, and a support table for a subject to be treated.

2. Description of the Prior Art

Therapy equipment of this type serve the purpose of treating stone pathologies (lithotripsy), treating tumors, or for treating bone conditions (osterorestoration). In the former instance, a shock wave source is usually provided as the source of focused acoustic waves. In the case of tumor treatment, for example, a pressure pulse source that generates negative pressure pulses (underpressure or rarefaction pulses) and/or an ultrasound source that continuously delivers ultrasound (hyperthermia) can be provided as the source of focused acoustic waves. A shock wave source is likewise normally provided as source of focused acoustic waves for the treatment of bone conditions.

Regardless of the purpose of the treatment, a subject to be treated with such a therapy station is aligned relative to the source of focused acoustic waves, with the assistance of the x-ray locating system, by adjusting the source carrier and the support table relative to one another, so that a region of the subject to be treated is located in the focus of the acoustic waves. The x-ray carrier is usually connected such to the source carrier so that it follows the motion of the latter, so that an effective check can be made at any time after the positioning of the region to be treated in the focus of the acoustic waves, to see whether the previously-made alignment of the subject to be treated relative to the focus is still present.

Quite a considerable structural outlay must be provided in known therapy means for realizing these requirements. In a therapy station disclosed, for example, in U.S. Pat. No. 5,044,354, the source carrier, the x-ray carrier and the support table are attached to a stand column pivotable around an axis either independently or in common, as desired. The patient support table is secured to a boom pivotable around the aforementioned axis and is adjustable relative to the boom in the direction of the axes of a spatial coordinate system. In order to be able to fashion the boom with adequate stability (this boom being loaded not only by the weight of the subject to be treated and of the patient support table but also by the weight of the drives required for its adjustment), a rather substantial structural outlay must be produced, resulting in substantial costs.

SUMMARY OF THE INVENTION

It is an object of the present invention to provide a therapy station of the type initially described which is constructed simply and, consequently, economically.

This object is achieved in accordance with the principles of the present invention in a therapy station for treatment of a subject with focused acoustic waves, having a source carrier to which a source of focused acoustic waves that generates acoustic waves converging in a focus is attached, an x-ray carrier to which an x-ray locating station having an x-ray radiator that generates an x-ray beam having a central ray and having a radiation receiver (such as an x-ray image intensifier) lying opposite thereto, and a patient support table for a subject to be treated, wherein the x-ray carrier is pivotably attached to the source carrier such that the central ray of the x-ray beam of the x-ray locating system always proceeds through the focus of the acoustic waves (the x-ray carrier is preferably pivotable around an axis proceeding through the focus) and wherein the source carrier is adjustable relative to the support table in one plane. As a consequence of the x-ray carrier being pivotably attached to the source carrier, and the source carrier being adjustable in one plane relative to the support table, a simplified, and thus more economical structure is achieved compared to the prior art.

To be able to bring a region to be treated into the focus of the acoustic waves, an adjustability of the support table and the source carrier in a direction intersecting the aforementioned plane is required in addition to the adjustability of the source carrier relative to the support table. This direction in the therapy station of the invention preferably proceeds substantially parallel to the support surface of the support table. In an embodiment of the invention, this direction intersects the aforementioned plane at a right angle.

In a preferred embodiment of the invention the support table is adjustable relative to the source carrier. Given an adjustment direction at a right angle relative to the plane of the support surface, this offers the advantage that the adjustability of the support table (which is required in this direction anyway in order to permit the patient to easily mount the patient bearing table, or to facilitate the placement of an immobile patient on the support table), simultaneously serves the purpose of positioning the region to be treated in the focus of the acoustic waves.

The source carrier can be adjustable along a straight line in the plane, in one direction that proceeds substantially transversely relative to the longitudinal axis of the support table, as well as in another direction which proceeds at substantially parallel to the longitudinal axis of the support table. The adjustability of the source carrier in the this plane thus can be realized in a simple and economical way.

Preferably the source carrier in the inventive therapy station has a box-shaped base having an open region which the radiation receiver of the x-ray locating system can be pivoted. A compact structure of the therapy station results derives, with further compactness when the source is accepted in the box-shaped base part of the source carrier at one side of the open region. Preferably, the source is movable from a standby position, wherein it is located substantially inside the base, to a working position in which the focus of the acoustic waves lies on the central ray of the x-ray locating system. Since the source is located substantially inside the box-shaped base of the source carrier in its standby position, it is assured that it does not represent an impediment when a patient mounts the support table or is placed thereon.

The box-shaped base of the source carrier may have a carrier section at the other side of the open region, the x-ray carrier being pivotably seated at this carrier section. This measure also promotes a compact structure of the therapy system.

DESCRIPTION OF THE DRAWINGS

An exemplary embodiment of a therapy station constructed in accordance with the principles of the present invention is schematically shown in the drawing in a perspective view.

DESCRIPTION OF THE PREFERRED EMBODIMENTS

The therapy system of the invention has a support table generally referenced 1 having a support plate 2, which is height-adjustable with reference to a base 5 by means of two telescoping columns 3 and 4 operated by a motor drive (not shown) in a known manner. The support plate 2 has a preferably horizontal upper side forming the supporting surface 6 for a patient to be treated.

A carriage 7 is seated on the base 5 so as to be adjustable along a straight line in the direction of the longitudinal axis of the support plate 2, that proceeds parallel to the x-axis of the spatial coordinate system shown in the figure. This adjustment is indicated with the double arrow referenced x.

A source carrier generally referenced 8 is seated longitudinally displaceable on the carriage 7 so as to be movable in a direction that proceeds transversely to the longitudinal axis of the support plate 2, and thus parallel to the z-axis of the spatial coordinate system. This adjustment is indicated by the double arrow z.

The bearing of the carriage 7 on the base 5 or the source carrier 8 on the carriage 7 ensue on the basis of known longitudinal guides that can be implemented as roller bearings or plain bearings. The source carrier 8 is thus adjustable in a plane proceeding parallel to the support surface 6. Since the height adjustment of the support plate 2 ensues in the direction of the double arrow y parallel to the y-axis of the coordinate system, the support plate 2 is adjustable relative to the source carrier 8 in a direction proceeding at a right angle to the aforementioned plane. The adjustment of the carriage 7, the support plate 2 and the source carrier 8 in the directions of the double arrows x, y or z ensues with suitable motors, particularly electric motors, in a known manner not shown in the drawing and, as necessary, using suitable gearings.

The source carrier 8 has a base member 9 which is essentially box-shaped and which extends between the telescoping columns 3 and 4 transversely under the support plate 2 of the support table 1. The base member 9 is subdivided into two sections 11 and 12 by an open region 10. One section 11 projects toward the front under the support plate 2 with reference to the illustration of the figure. The section 12 projects outwardly from under the support plate 2 toward the rear.

A source 13 of focused acoustic waves is attached to the section 11 of the base member 9 of the source carrier 8, such that its application end projects from the section 11 in its working position (which is shown in the drawing). The focus of the acoustic waves thereby assumes the position referenced F in the drawing. In its working position, the source 13 projects through an opening 14 of the support plate 2 that can be closed as needed by a plate (not shown). The opening 14 is provided for enabling contact of the application end of the source 13 to the body surface of a patient lying on the support plate 2.

The section 12 of the base member 9 of the source carrier 8 is provided with a vertically directed projection 15 to which a U-shaped x-ray carrier 16 is pivotally mounted so as to be motor-pivoted in the direction of the curved double arrow "α" around an axis A that proceeds substantially parallel to the seating surface 6, and at a right angle relative to the longitudinal axis of the support plate 2, as well as through the focus F. The corresponding drive means that contains known motors and may contain gearings is not shown in the figure.

The x-ray radiator 17 and the radiation receiver, namely an x-ray image intensifier 18, forming an x-ray locating system, are attached to the x-ray carrier 16. The central ray Z of the x-ray beam emanating from the x-ray radiator 17 attached to the upper end of the x-ray carrier 16 proceeds through the focus F and thus intersects the axis A around which the x-ray carrier 16 is pivotable. It is thus assured that the central ray Z proceeds through the focus F for any desired pivoted positions of the x-ray carrier 16 relative to the source 13. The x-ray image intensifier 18, moreover, is located within the open region 10 when the x-ray carrier 16 is vertically aligned and is pivoted out of the open region 10 in either direction when the x-ray carrier 16 is pivoted.

For the implementation of a treatment, the source 13 is first retracted into a standby position wherein it is completely located within the section 11 of the base member 9 of the source carrier 8 as indicated with broken lines in the figure. Subsequently, the source carrier 8 is pushed in the direction of the z-axis as far as possible under the support plate 2, which is moved into its lowest position in the direction of the y-axis. A patient can then easily mount the support plate 2, or can be easily placed on the support plate 2 by attending personnel. The source 13 is now brought into its working position in which it has its application end pressing against the body surface of the patient, under pressure.

Subsequently, the x-ray carrier 16 is brought into its vertical position wherein the central ray Z of the x-ray beam proceeds parallel to the y-axis. The x-ray locating system is then activated and the source carrier 8 is displaced in the directions of the x-axis and the z-axis so that the image of the region to be treated coincides with a mark in the x-ray image shown on a monitor. This mark corresponds in a known way to the projection of the focus F into the image plane of the x-ray image. When the source carrier 8 is aligned in the described way, the region to be treated lies on the central ray Z of the x-ray beam. The x-ray carrier 16 is now pivoted in one or other direction indicated by the double arrow "α", whereby the pivot direction is selected dependent on which of the two pivot directions in the current treatment case leads one to expect a better x-ray presentation of the region to be treated. The x-ray locating system is re-activated and the support plate 2 is adjusted in height in the direction of the y-axis such that the image of the region to be treated again coincides with the mark in the x-ray image shown on the monitor. The region to be treated is now located in the focus F of the acoustic waves. For reliability, there is the possibility of rechecking the alignment of the patient and the source carrier 8 relative to one another when the central ray of the x-ray locating system is vertically directed, in order to be able to correct potential dislocations.

After the alignment of patient and source carrier 8 relative to one another has ensued in the described way, the region to be treated can be charged with acoustic waves.

The source 13, for example, can be a focused shock wave source as disclosed in U.S. Pat. No. 4,674,505 and in European Application 0 188 750. Given employment of such a shock wave source, there is the possibility of treating stone and bone conditions. However, a pressure pulse source as disclosed, for example, in German Utility Model 91 09 025 can alternatively be provided as source 13. Such a source emits negative pressure pulses and is particularly suitable for treating tumors. Further, a therapeutic ultrasound source can be provided as the source 13, which emits therapeutic ultrasound in continuous form for treating tumors. Moreover, sources as disclosed, for example, in U.S. Pat. No. 4,926,857 and U.S. Pat. No. 4,976,255 can be provided as the source 13 for treating tumors, which combine a pressure pulse source and a therapeutic ultrasound source.

Independently of the source 13 employed, there is the possibility of integrating an ultrasound locating system therein in a known way. Such an ultrasound locating system may be either an ultrasound B-scanner or an ultrasound echo locating system.

Independently of the type of source 13, its application end is provided with an application bellows 19 that terminates a space inside the source 13 that is filled with a suitable acoustic propagation medium and serves the purpose of pressing the source 13 against the body surface of the respective patient for acoustic coupling. This ensues when, after the patient has been placed on the support plate 2, the source 13 is brought into its working position.

The therapy station of the invention has the advantage of a structurally simple, and thus economical structure. The compact structure is further enhanced by the fashioning of the source carrier 8 with the open region 10. The operating elements required for the operation of the therapy station can be attached to the slanting portion 20. The base 9, moreover, can accept all required supply units for the source 13, as well as the units required for the operation of the x-ray locating system. Only a monitor for displaying the x-ray images is then still required as an additional element. This can be secured (in a way that is not shown) to an adjustable carrying arm attached, for example, to the source carrier 8.

Although modifications and changes may be suggested by those skilled in the art, it is the intention of the inventors to embody within the patent warranted hereon all changes and modifications as reasonably and properly come within the scope of their contribution to the art.

We claim as our invention:

1. A therapy station for treating a subject with focused acoustic waves comprising:
   a source of focused acoustic waves, said focused acoustic waves converging at a focus;
   a support table adapted to accommodate a subject to be treated;
   source carrier means, to which said source of focused acoustic waves is mounted,
      for adjusting the position of said source of focused acoustic waves in a plane relative to said support table;
   x-ray locating means for identifying the position of a treatment site in said subject, and having a central ray; and
   x-ray carrier means, to which said x-ray locating means is mounted and which is pivotably attached to said source carrier means, for permitting rotation of said x-ray locating means relative to said source of focused acoustic waves while maintaining said central ray proceeding through said focus.

2. A therapy station as claimed in claim 1 further comprising means for adjusting said support table and said source carrier means relative to each other in a direction intersecting said plane at a right angle.

3. A therapy station as claimed in claim 2 wherein said support table has a support surface, and wherein said plane proceeds substantially parallel to said support surface.

4. A therapy station as claimed in claim 2 wherein said means for adjusting said support table and said source carrier means relative to each other comprises means for adjusting said support table relative to said source carrier means.

5. A therapy station as claimed in claim 1 wherein said support table has a longitudinal axis, and wherein said source carrier means includes means for adjusting said source carrier means along a straight line in said plane in a direction substantially transverse to said longitudinal axis of said support table and in a direction which is substantially parallel to said longitudinal axis of said support table.

6. A therapy station as claimed in claim 1 wherein said x-ray locating means includes a radiation receiver, and wherein said source carrier means comprises a box-shaped base having an open region into which said radiation receiver of said x-ray locating means is provided by said x-ray carrier means.

7. A therapy station as claimed in claim 6 wherein said source of acoustic waves is disposed in said base of said source carrier means at one side of said open region.

8. A therapy station as claimed in claim 7 wherein said source carrier means includes means for moving said source of acoustic waves from a standby position wherein said source of acoustic waves is substantially completely contained within said base into a working position wherein said focus is intersected by said central ray of said x-ray locating means.

9. A therapy station as claimed in claim 7 wherein said base has a carrier section to which said x-ray carrier means is pivotably attached.

* * * * *